United States Patent
Guenoun et al.

(10) Patent No.: US 11,040,000 B2
(45) Date of Patent: Jun. 22, 2021

(54) PROCESS FOR MANUFACTURING OMNIPHOBIC COSMETIC PIGMENTS

(71) Applicants: COMMISSARIAT À L'ÉNERGIE ATOMIQUE ET AUX ÉNERGIES ALTERNATIVES (CEA), Paris (FR); CENTRE NATIONAL DE LA RECHERCHE SCIENTIFIQUE, Paris (FR); MIYOSHI EUROPE S.A.S., Saint-Priest (FR)

(72) Inventors: Patrick Guenoun, Gif-sur-Yvette (FR); Christophe Fajolles, Gif-sur-Yvette (FR); Tetsuya Takahashi, Saint-Priest (FR); Stephane Nicolas, Saint-Priest (FR); Pauline Bosmet, Saint-Priest (FR); Sébastien Gougeon, Saint-Priest (FR)

(73) Assignees: COMMISSARIAT À L'ÉNERGIE ATOMIQUE ET AUX ÉNERGIES ALTERNATIVES (CEA), Paris (FR); CENTRE NATIONAL DE LA RECHERCHE SCIENTIFIQUE, Paris (FR); MIYOSHI EUROPE S.A.S., Saint-Priest (FR)

( * ) Notice: Subject to any disclaimer, the term of this patent is extended or adjusted under 35 U.S.C. 154(b) by 0 days.

(21) Appl. No.: 16/684,802

(22) Filed: Nov. 15, 2019

(65) Prior Publication Data
US 2020/0155441 A1 May 21, 2020

(30) Foreign Application Priority Data
Nov. 15, 2018 (EP) .................................. 18306498

(51) Int. Cl.
*A61K 8/73* (2006.01)
*A61K 8/29* (2006.01)
*A61K 8/36* (2006.01)
*A61K 8/02* (2006.01)

(52) U.S. Cl.
CPC ............... *A61K 8/736* (2013.01); *A61K 8/29* (2013.01); *A61K 8/36* (2013.01); *A61K 8/02* (2013.01); *A61K 2800/31* (2013.01); *A61K 2800/412* (2013.01)

(58) Field of Classification Search
None
See application file for complete search history.

(56) References Cited

FOREIGN PATENT DOCUMENTS

| CN | 102489264 A | * | 6/2012 | .............. B01J 20/24 |
| CN | 104311888 A | * | 1/2015 | ................ C08L 5/08 |
| JP | S62-223108 A | | 10/1987 | |
| JP | S62223108 A | * | 10/1987 | ............. A61K 7/021 |
| WO | 98/22540 A1 | | 5/1998 | |
| WO | 2010/128204 A1 | | 11/2010 | |
| WO | 2014/081322 A1 | | 5/2014 | |

* cited by examiner

*Primary Examiner* — Brian J Davis
(74) *Attorney, Agent, or Firm* — Maier & Maier, PLLC

(57) ABSTRACT

For the cosmetic field, omniphobic cosmetic pigments under the form of a core shell structure: the core is or includes of a metal oxide on which is adsorbed poly($\beta$-(1→4)-D-glucosamine) chains; the chains being acetylated, or partially or totally deacetylated. Also, the process for manufacturing the omniphobic cosmetic pigments, including:
(i) preparing an acidic aqueous solution including metal oxide particles and a poly ($\beta$-(1→4)-D-glucosamine), the poly ($\beta$-(1→4)-D-glucosamine) being acetylated, or partially or totally deacetylated; and
(ii) increasing the pH until 12, of the solution obtained at step (i) in order to obtain the adsorption of said poly ($\beta$-(1→4)-D-glucosamine on the metal oxide particles and the precipitation of the resulting metal oxide particles coated with the poly ($\beta$-(1→4)-D-glucosamine.

18 Claims, 2 Drawing Sheets

PROCESS FOR MANUFACTURING OMNIPHOBIC COSMETIC PIGMENTS

FIELD

The present invention relates to the cosmetic field. Especially, the present invention refers to omniphobic cosmetic pigments under the form of a core shell structure: the core comprises or consists of a metal oxide on which is adsorbed poly(β-(1→4)-D-glucosamine) chains; said chains being acetylated, partially or totally deacetylated. The present invention also relates to the process for manufacturing said omniphobic cosmetic pigments, and their uses.

BACKGROUND

In cosmetics, the use of inorganic pigments is widespread because of the various properties they bring to the products.

Inorganic cosmetic pigments are mainly metal oxides such as titanium dioxide ($TiO_2$), iron oxides (for example, $Fe_3O_4$) or hydroxylated magnesium silicate.

Whatever the pigment, the consumer is looking for an optimal hold of the pigment on his skin. However, the skin is a complex organ that secretes both sebum (comparable to a fatty medium) and sweat (comparable to an aqueous medium).

Consequently, there is still a need for providing optimized cosmetic pigments for long lasting the hold of said pigments on the skin of the consumer. Especially, there is a need for providing omniphobic cosmetic pigments, that is to say a pigment suitable for human's skin that may both resist to sebum and sweat, meaning that the two latter liquids should not spread onto the pigments.

Some attempts have been carried out by modifying the surface of metal oxide particles with fluorinated compounds such as perfluorooctanoic acid (PFOA). However, recent studies have highlighted an increased risk of cancer development due to fluorinated compounds, and a negative impact on the environment.

Thus, there is an urgent need for providing omniphobic cosmetic pigments while avoiding fluorinated molecules as described above.

Surprisingly, the Applicant has evidenced that cosmetic pigments comprising a metal oxide core on which are adsorbed poly(β-(1→4)-D-glucosamine) chains, partially or totally N-acetylated, have omniphobic properties. The cosmetic pigments of the invention are manufactured thanks to a specific process that implies a precipitation step by abrupt modification of the pH of the reaction medium.

SUMMARY

The present invention relates to a process for manufacturing an omniphobic cosmetic pigment, said process comprising:
(i) Preparing an acidic aqueous solution comprising metal oxide particles and a poly(β-(1→4)-D-glucosamine), said poly(β-(1→4)-D-glucosamine) being acetylated, or partially or totally deacetylated; and
(ii) Increasing the pH until about 12, of the solution obtained at step (i) in order to obtain the adsorption of said poly(β-(1→4)-D-glucosamine) on the metal oxide particles and the precipitation of the resulting metal oxide particles coated with said poly(β-(1→4)-D-glucosamine).

According to one embodiment, the metal oxide particles are selected from titanium oxide, iron oxide, zinc oxide, zirconium oxide, yellow iron oxide, black iron oxide, red iron oxide, chromium oxide, chromium hydroxide, ultramarine, silicates such as mica, sericite, kaolin, talc, aluminium silicate, magnesium silicate, calcium silicate or clay; preferably are titanium oxide particles.

According to one embodiment, the metal oxide particles have a size ranging from 100 nm to 100 μm; preferably ranging from 500 nm to 60 μm.

According to one embodiment, the poly (β-(1→4)-D-glucosamine) is partially N-deacetylated; preferably is chitosan. According to one embodiment, the poly(β-(1→4)-D-glucosamine) is either totally deacetylated or both deacetylated and acetylated; preferably is chitosan.

According to one embodiment, the poly(β-(1→4)-D-glucosamine) has a viscosity measured at about 25° C., ranging from 10 cP to 2000 cP; preferably from 40 cP to 800 cP; more preferably from 50 cP to 350 cP.

According to one embodiment, the poly(β-(1→4)-D-glucosamine) is partially deacetylated and has a deacetylation degree ranging from 70% to 99%; preferably from 75% to 95%; more preferably ranges from 75% to 85%.

According to one embodiment, the poly (β-(1→4)-D-glucosamine) has a mass average molar mass (Mw) ranging from 40 000 Da to 500 000 Da; preferably from 100 000 Da to 300 000 Da.

According to one embodiment, the amount of the poly (β-(1→4)-D-glucosamine) ranges from more than 0% to 20%; preferably from 1% to 15%; more preferably is about 3% or 10%, by weight to the total weight of said poly (β-(1→4)-D-glucosamine) and metal oxide particles.

According to one embodiment, the acidic aqueous solution comprises an acid; preferably an organic acid; more preferably acetic acid.

The present invention relates to an omniphobic cosmetic pigment obtained by the process of the invention.

According to one embodiment, the omniphobic cosmetic pigment comprises or consists of titanium oxide particles on which are adsorbed chitosan chains.

The present invention relates to a cosmetic composition comprising the omniphobic cosmetic pigment of the invention and a cosmetically acceptable base.

According to one embodiment, the cosmetically acceptable base is anhydrous.

According to one embodiment, the composition is under the form of an aqueous gel, an oily gel, a paste, a cream, a lotion, a milk, a stick, a soap, a foam, a shampoo, a compact powder, a loose powder, a nail polish, a beauty mask, an aerosol, a film, a serum, an emulsion, or a patch.

The present invention relates to a cosmetic skin improvement method comprising using the omniphobic cosmetic pigment or the cosmetic composition of the invention, in a subject in need thereof.

According to one embodiment, the composition is administered to the skin of a subject in need thereof, once per day.

The present invention relates to the use of the cosmetic composition of the invention, in make-up, skincare, sun care, haircare, nail polish, toiletries, baby care or pet care.

DETAILED DESCRIPTION

Figure 1:
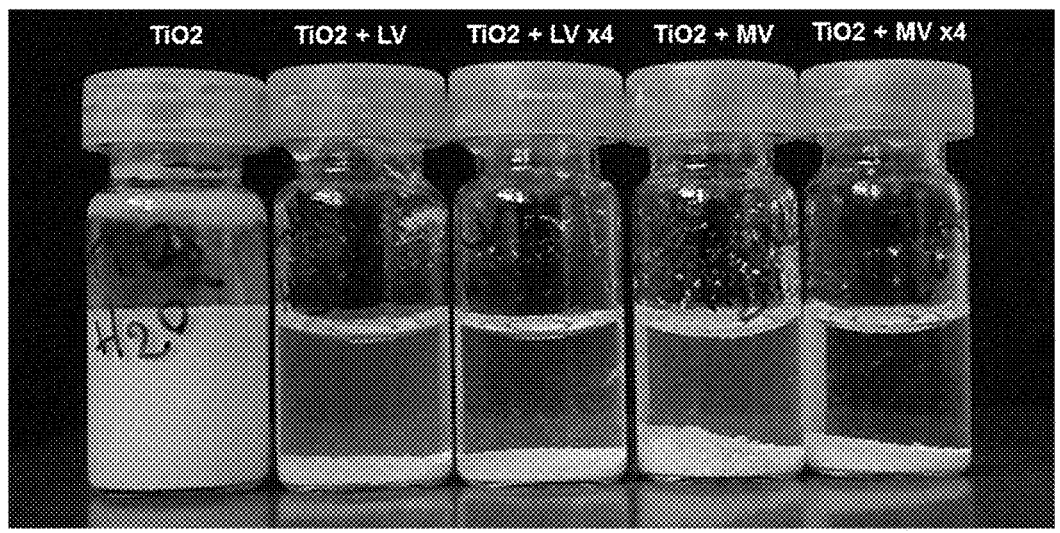
FIG. 1 is a photograph showing from left to right, vials containing pure water and: uncoated $TiO_2$ particles [$TiO_2$]; $TiO_2$ particles coated with chitosan A and washed once [$TiO_2$+LV]; $TiO_2$ particles coated with chitosan A and washed four times [$TiO_2$+LV×4]; $TiO_2$ particles coated with chitosan B and washed once [TiO$_2$+MV] and TiO$_2$ particles coated with chitosan B and washed four times [TiO$_2$+MV×4].

In the present invention, the following terms have the following meanings:

"About": preceding a figure means plus or less 10% of the value of said figure.

"Acetic acid" or "ethanoic acid": refers to an organic compound of formula CH$_3$—COOH.

"Acid": refers to any compound able of releasing hydrogen ions (H$^+$) (Brönsted acid) or able of forming a covalent bond with an electron pair (Lewis acid).

"Adsorption": refers to a surface phenomenon by which atoms, ions or molecules (adsorbates) bind to a solid surface (adsorbent) from a gas phase, liquid or solid solution.

"Anhydrous composition": refers to a composition which comprises less than 5% by weight of water, preferably less than 2% by weight of water, indeed even less than 0.5% of water, with respect to its total weight, and in particular a composition which is devoid of water.

"Chitin": refers to a natural polysaccharide which is a poly (β-(1→4)-N-acetyl-D-glucosamine) Especially, "chitin" refers to a polysaccharide of formula:

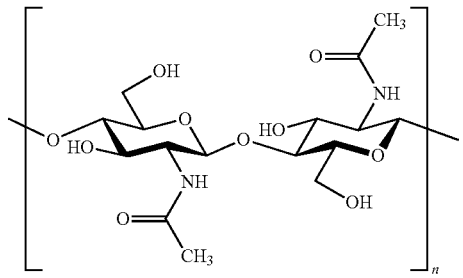

wherein n is a positive integer, preferably ranging from 10 from 2 000.

"Chitosan": refers to a polysaccharide which is a random copolymer of β-(1→4)-N-acetyl-D-glucosamine and of β-(1→4)-D-glucosamine (i.e. a poly[(β-(1→4)-N-acetyl-D-glucosamine)-co-(β-(1→4)-D-glucosamine)]). The term "chitosan" may also refers to a deacetylated poly (β-(1→4)-D-glucosamine)

"Cosmetic": refers to the use in order to improve the esthetic appearance or increase comfort of the body of a subject. According to one embodiment, the term "cosmetic" includes solar care such as the use of solar creams.

"Cosmetically acceptable base": relates to any compound for use in contact with the epidermis and/or the dermis, and which does not provoke any side effects such as toxicity, irritation, inflammation or allergic response. In the present invention, a cosmetically acceptable base includes base for topical administration. According to one embodiment, the expression "cosmetically acceptable base" refers to a carrier in which is dispersed the pigment, and that is for use in contact with the epidermis and/or the dermis, and which does not provoke any side effects such as toxicity, irritation, inflammation or allergic response.

"Chitosan acetylation degree (DA)": refers to the percentage of N-acetylated units compared to the total number of units in the backbone of a chitosan.

"Chitosan deacetylation degree (DD)": refers to the percentage of N-deacetylated units compared to the total number of units in the backbone of a chitosan.

"Cosmetic skin improvement method": refers to any cosmetic method allowing to improve the esthetic appearance of the skin of a subject.

"Iron oxide": refers to a chemical compound made of oxygen and iron atoms. According to one embodiment, "iron oxide" refers to compounds of formula: FeO, Fe$_3$O$_4$ or Fe$_2$O$_3$.

"Metal oxide": refers to any chemical compounds made of metal and oxygen. According to one embodiment, the expression "metal oxide" refers to any compound having an anionic moiety which is an oxide and a metallic cationic moiety.

"Omniphobic": refers to a chemical compound or material having the properties to both being hydrophobic and oleophobic. According to one embodiment, the term "omniphobic" refers to a compound or a material, able to be very little wetted by the sebum and sweat secreted by the skin of a subject.

"Particle": refers to a compound under a spherical or spheroid form. According to one embodiment, the term "particle" in the invention refers to a spherical or spheroid pigment.

"pH": refers in chemistry, to a scale for measuring the acidity of a solution. According to one embodiment, pH refers to a scale for measuring the acidity of an aqueous solution, preferably ranging from 0 to 14.

"Pigment": refers to a chemical coloring substance insoluble in the medium which it colors, and under the form of fine dispersible and non-agglomerated particles.

"Poly (β-(1-4)-D-glucosamine)": refers to a polysaccharide resulting from the polymerization of D-glucosamine units, in which two consecutive units are covalently linked together by a β,1-4, glycosidic bond. According to one embodiment, the term "poly(β-(1-4)-D-glucosamine)" includes poly(β(1-4)-N-acetyl-D-glucosamine) (also called "chitin") and partially or totally deacetylated poly(β(1-4)-N-acetyl-D-glucosamine) (also called "chitosan").

"Precipitation": refers to the emergence of an insoluble solid obtained from a liquid solution.

"Particle size": refers to the mean diameter of a particle. According to the invention, the particle size (or mean diameter of a particle) is measured by Dynamic Light Scattering (DLS), preferably with the Malvern Zetasizer®.

"Subject": refers to a mammal, preferably a human, receiving the particles of the invention.

"Titanium oxide": refers to a chemical compound made of oxygen (O) and titanium (Ti) atoms. According to one embodiment, the terms "titanium oxide" refer to titanium dioxide ($TiO_2$), titanium (III) oxide ($Ti_2O_3$) or titanium (II) oxide (TiO), preferably refers to titanium dioxide ($TiO_2$).

"Viscosity": refers to the measure (expressed in centipoise (cP)) of a substance's resistance to speed under an applied force per unit surface. According to one embodiment, the viscosity is measured at a temperature of about 20° C. or 25° C.

Process

This invention relates to a process for manufacturing cosmetic pigments. According to one embodiment, the invention relates to a process for manufacturing hydrophobic and/or oleophobic pigments. According to one embodiment, the invention relates to a process for manufacturing both hydrophobic and oleophobic pigments (i.e. omniphobic pigments).

According to one embodiment, the process of the invention comprises a step for preparing an acidic aqueous solution comprising or consisting of metal oxide particles and a poly (β-(1→4)-D-glucosamine), said poly (β-(1→4)-D-glucosamine) being optionally partially or totally N-deacetylated (step (i)).

According to one embodiment, the poly (β-(1→4)-D-glucosamine) is partially or totally deacetylated from poly (β-(1→4)-N-acetyl glucosamine).

According to one embodiment, the process of the invention further comprises a step of increasing the pH until about 12, of the solution obtained at step (i) (step (ii)). According to one embodiment, the process of the invention further comprises a step of increasing the pH in a range from 11 to 13, preferably from in a range 11.5 to 12.5, more preferably of 12, of the solution obtained at step (i) (step (ii)).

According to one embodiment, the step (ii) leads to the adsorption of said poly (β-(1→4)-D-glucosamine) on the metal oxide particles. According to one embodiment, the step (ii) leads to the precipitation of metal oxide particles coated, preferably by adsorption, with said poly (β-(1→4)-D-glucosamine).

Step (i)

According to one embodiment, the solution of step (i) comprises pure water. According to one embodiment, the solution of step (i) comprises deionized water.

According to one embodiment, the solution of step (i) comprises an acid. According to one embodiment, the solution of step (i) comprises a Lewis acid. According to one embodiment, the solution of step (i) comprises a Brönsted acid. According to one embodiment, the solution of step (i) comprises an organic acid, preferably a carboxylic acid such as, but not limited to, methanoic acid, ethanoic acid (or acetic acid), propanoic acid, butanoic acid, pentanoic acid, hexanoic acid or heptanoic acid.

According to one embodiment, the solution of step (i) has a pH lower than 7, preferably ranging from 0 to 6.

According to one embodiment, the metal oxide particles are selected from titanium oxide, iron oxide, zinc oxide, zirconium oxide, yellow iron oxide, black iron oxide, red iron oxide, chromium oxide, and chromium hydroxide; preferably are titanium oxide particles.

According to one embodiment, the metal oxide particles have a size ranging from 10 nm to 100 µm, preferably ranging from 20 nm to 100 µm, from 30 nm to 100 µm, from 40 nm to 100 µm, from 50 nm to 100 µm, from 60 nm to 100 µm, from 70 nm to 100 µm, from 80 nm to 100 µm, from 90 nm to 100 µm, from 100 nm to 100 µm, from 110 nm to 100 µm, from 120 nm to 100 µm, from 130 nm to 100 µm, from 140 nm to 100 µm, from 150 nm to 100 µm, from 160 nm to 100 µm, from 170 nm to 100 µm, from 180 nm to 100 µm, from 190 nm to 100 µm, from 200 nm to 100 µm, from 250 nm to 100 µm; from 300 nm to 100 µm, from 350 nm to 100 µm, from 400 nm to 100 µm, from 450 nm to 100 µm, from 500 nm to 100 µm, from 550 nm to 100 µm, from 600 nm to 100 µm, from 650 nm to 100 µm, from 700 nm to 100 µm, from 750 nm to 100 µm, from 800 nm to 100 µm, from 850 nm to 100 µm, from 900 nm to 100 µm, from 950 nm to 100 µm, or from 1000 nm to 100 µm.

According to one embodiment, the metal oxide particles have a size ranging from 1 µm to 100 µm; preferably ranging from 20 µm to 60 µm; more preferably are about 40 µm.

According to one embodiment, the metal oxide particles have a size ranging from 1 µm to 100 µm; preferably from 1 µm to 90 µm, from 1 µm to 80 µm, from 1 µm to 70 µm, from 1 µm to 60 µm, from 1 µm to 50 µm, from 1 µm to 40 µm, from 1 µm to 30 µm, from 1 µm to 20 µm, or from 1 µm to 10 µm. According to one embodiment, the metal oxide particles have a size ranging from 10 µm to 100 µm; preferably from 20 µm to 100 µm, from 30 µm to 100 µm, from 40 µm to 100 µm, from 50 µm to 100 µm, from 60 µm to 100 µm, from 70 µm to 100 µm, from 80 µm to 100 µm, or from 90 µm to 100 µm. According to one embodiment, the metal oxide particles have a size of about 5, 10, 15, 20, 25, 30, 35, 40, 45, 50, 55, 60, 65, 70, 75, 80, 85, 90, 95 or 100 µm.

According to one embodiment, the poly (β-(1→4)-D-glucosamine) is poly (β-(1→4)-N-acetyl-D-glucosamine)N-acetylated.

According to one embodiment, the poly (β-(1→4)-D-glucosamine) partially N-deacetylated is a random copolymer of β-(1→4)-N-acetyl-D-glucosamine and of (β-(1→4)-D-glucosamine (i.e. a poly[(β-(1→4)-N-acetyl-D-glucosamine)-co-(β-(1→4)-D-glucosamine)]).

According to one embodiment, the poly (β-(1→4)-D-glucosamine), partially N-deacetylated, has a deacetylation degree ranging from more than 50% to 99%; preferably from 75% to 95%; more preferably ranges from 75% to 85%. According to one embodiment, the deacetylation degree ranges from more than 50% to 90%; preferably from more than 50% to 80%; from more than 50% to 70%; or from more than 50% to 60%. According to one embodiment, the deacetylation degree ranges from 60% to 100%; preferably from 70% to 100%, from 80% to 100%, or from 90% to 100%. According to one embodiment, the deacetylation degree is about 55, 60, 65, 70, 75, 80, 85, 90, 95 or 100%.

According to one embodiment, the poly (β-(1→4)-D-glucosamine) has mass average molar mass (Mw) ranging from 10 000 Da to 500 000 Da; preferably from 30 000 Da to 300 000 Da; more preferably from 40 000 Da to 200 000 Da. According to one embodiment, the poly (β-(1→4)-D-glucosamine) has mass average molar mass (Mw) ranging from 40 000 Da to 500 000 Da; preferably from 50 000 Da to 400 000 Da. According to one embodiment, the poly (β-(1→4)-D-glucosamine) has mass average molar mass (Mw) ranging from 40 000 Da to 400 000 Da; preferably from 40 000 Da to 350 000 Da, from 40 000 Da to 300 000 Da, from 40 000 Da to 250 000 Da, from 40 000 Da to 200 000 Da, from 40 000 Da to 150 000 Da, from 40 000 Da to 100 000 Da, or from 40 000 Da to 50 000 Da. According to one embodiment, the poly (β-(1→4)-D-glucosamine) has a mass average molar mass (Mw) ranging from 50 000 Da to 400 000 Da; preferably from 60 000 Da to 400 000 Da, from 70 000 Da to 400 000 Da, from 80 000 Da to 400 000 Da, from 90 000 Da to 400 000 Da, from 100 000 Da to 400 000

Da, from 110 000 Da to 400 000 Da, from 120 000 Da to 400 000 Da, from 130 000 Da to 400 000 Da, from 140 000 Da to 400 000 Da, from 150 000 Da to 400 000 Da, from 160 000 Da to 400 000 Da, from 170 000 Da to 400 000 Da, from 180 000 Da to 400 000 Da, from 190 000 Da to 400 000 Da, from 200 000 Da to 400 000 Da, from 210 000 Da to 400 000 Da, from 220 000 Da to 400 000 Da, from 230 000 Da to 400 000 Da, from 240 000 Da to 400 000 Da, from 250 000 Da to 400 000 Da, from 260 000 Da to 400 000 Da, from 270 000 Da to 400 000 Da, from 280 000 Da to 400 000 Da, from 290 000 Da to 400 000 Da, from 300 000 Da to 400 000 Da, from 310 000 Da to 400 000 Da, from 320 000 Da to 400 000 Da, from 330 000 Da to 400 000 Da, from 340 000 Da to 400 000 Da, from 350 000 Da to 400 000 Da, from 360 000 Da to 400 000 Da, from 370 000 Da to 400 000 Da, from 380 000 Da to 400 000 Da or 390 000 Da to 400 000 Da. According to one embodiment, the poly ($\beta$-(1→4)-D-glucosamine) has a mass average molar mass (Mw) ranging from 50 000 Da to 190 000 Da. According to one embodiment, the chitosan has a mass average molar mass (Mw) ranging from 50 000 Da to 190 000 Da (chitosan A). According to one embodiment, the poly ($\beta$-(1→4)-D-glucosamine) has a mass average molar mass (Mw) ranging from 310 000 Da to 380 000 Da.

According to one embodiment, the poly($\beta$-(1→4)-D-glucosamine) has a viscosity measured at about 25° C., ranging from 10 cP to 2000 cP; preferably from 40 cP to 800 cP; more preferably from 50 cP to 350 cP. According to one embodiment, the poly($\beta$-(1→4)-D-glucosamine) has a viscosity measured at about 25° C., ranging from 20 cP to 300 cP, from 200 cP to 800 cP or from 800 cP to 2000 cP. According to one embodiment, the poly($\beta$-(1→4)-D-glucosamine) has a viscosity measured at about 25° C., of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990 or 2000 cP.

According to one embodiment, the mass ratio of metal oxide particles to the poly 03-(1→4)-D-glucosamine), optionally partially or totally deacetylated, ranges from more than 0 to 20; preferably from 1 to 15; more preferably is about 10. According to one embodiment, the mass ratio of metal oxide particles to the poly ($\beta$-(1→4)-D-glucosamine), optionally partially or totally deacetylated, is about 1, 2, 3, 4, 5, 6, 7, 8, 9, 10, 11, 12, 13, 14, 15, 16, 17, 18, 19 or 20.

According to one embodiment, the amount of the poly ($\beta$-(1→4)-D-glucosamine), optionally partially or totally deacetylated, ranges from more than 0% to 20%; preferably from 1% to 15%; more preferably is about 3% or 10% by weight to the total weight of said poly ($\beta$-(1→4)-D-glucosamine) and metal oxide particles. According to one embodiment, the amount of the poly ($\beta$-(1→4)-D-glucosamine), optionally partially or totally deacetylated, is about 1, 2, 3, 4, 5, 6, 7, 8, 9, 10, 11, 12, 13, 14, 15, 16, 17, 18, 19 or 20 wt. % to the total weight of said poly ($\beta$-(1→4)-D-glucosamine) and metal oxide particles.

According to one embodiment, the chitosan in the solution ranges from 1% to 10%, preferably is 3% or 10%, by weight to the total weight of chitosan and $TiO_2$ particles. According to one embodiment, the chitosan in the solution is 1%, 2%, 3%, 4%, 5%, 6%, 7%, 8%, 9% or 10% by weight to the total weight of chitosan and $TiO_2$ particles.

According to one embodiment, the step (i) is carried out at a temperature ranging from 1° C. to 40° C., preferably ranging from 10° C. to 30° C.; more preferably of about 20° C. According to one embodiment, the step (i) is carried out at a temperature of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C.

Step (ii)

According to one embodiment, the step (ii) comprises or consists of increasing the pH of the solution obtained at step (i) as described above.

According to one embodiment, increasing the pH of the solution is implemented with a hydroxide, preferably hydroxide potassium, more preferably with a solution of potassium hydroxide at a concentration of about 1 mol/L.

According to one embodiment, the increasing of the pH of the solution obtained at step (i) as described above, is increased until about 12, 13 or 14.

According to one embodiment, the step (ii) does not comprise nor consist of increasing the pH of the solution obtained at step (i) for obtaining a pH lower than 12.

According to one embodiment, the step (ii) is carried out at a temperature ranging from 1° C. to 40° C., preferably ranging from 10° C. to 30° C.; more preferably of about 20° C. According to one embodiment, the step (ii) is carried out at a temperature of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C.

According to one embodiment, the step (ii) does not comprise heating. According to one embodiment, the step (ii) does not comprise heating at a temperature higher than 40° C., 50° C., 60° C., 70° C., 80° C., 90° C. or 100° C.

Other Steps

According to one embodiment, the process of the invention further comprises a washing step. According to one embodiment, washing is carried out with water.

According to one embodiment, the process of the invention further comprises a drying step. According to one embodiment, drying is carried out at a temperature ranging from 20° C. to 70° C.; preferably from 30° C. to 60° C.; more preferably from 40° C. to 55° C.

According to one embodiment, the process of the invention provides metal oxide particles on which are adsorbed chains of poly ($\beta$-(1→4)-D-glucosamine), optionally partially or totally deacetylated. According to one embodiment, the process of the invention provides pigment particles under the form of a powder. According to one embodiment, the process of the invention provides individualized pigment particles.

Pigment

The invention also relates to a cosmetic pigment. According to one embodiment, the cosmetic pigment is hydrophobic and/or oleophobic. According to one embodiment, the cosmetic pigment is both hydrophobic and oleophobic (i.e. the pigment is omniphobic).

According to one embodiment, the cosmetic pigment comprises or consist of a metal oxide particle on which is adsorbed a poly (β-(1→4)-D-glucosamine), optionally partially or totally deacetylated. According to one embodiment, the cosmetic pigment comprises or consist of a metal oxide particle on which is adsorbed a poly (β-(1→4)-N-acetyl-D-glucosamine), optionally partially or totally deacetylated. According to one embodiment, the cosmetic pigment comprises or consist of metal oxide particle on which are adsorbed chains of poly (β-(1→4)-D-glucosamine), optionally partially or totally deacetylated.

According to one embodiment, the cosmetic pigment, preferably omniphobic, is obtainable by the process of the invention as defined above.

Cosmetic Composition

The invention also relates to a composition comprising the cosmetic pigment as defined above. Especially, the invention relates to a composition comprising the cosmetic pigment, preferably omniphobic, obtainable by the process of the invention as defined above.

According to one embodiment, the composition is a cosmetic composition. According to one embodiment, the composition comprises a cosmetically acceptable base. According to one embodiment, the cosmetically acceptable base is under the form of a gel, a paste, a cream, a lotion, a milk, a stick, a shampoo, a powder, an aerosol, a film or a patch.

According to one embodiment, the amount of the cosmetic pigment in the composition ranges from more than 0% to 90%, by weight to the total weight of the composition.

According to the present invention, the compositions of the invention may be used in combination of at least one cosmetic agent selected from fatty acids, organic solvents, gelling agents, softening agents, surfactants, detergents, gelling agents, fragrances, emulsifying agents, opacifying agents, stabilizing agents, foaming agents, chelating agents, preservative agents, sunscreens, essential oils, dyes, mineral loads, or any compound used in cosmetics.

According to the present invention, the compositions of the invention may be used in combination of at least one active ingredient.

Skin Improvement Method

The invention also relates to a skin improvement method comprising using a cosmetic composition as defined above.

According to one embodiment, the skin improvement method comprises applying on the skin of a subject in need thereof, the cosmetic composition as defined above in a sole application. According to one embodiment, the cosmetic composition of the invention is applied on the skin of a subject in need thereof, at least once a month, preferably, twice a month; more preferably, once a week; more preferably, the composition of the invention is applied only once a week. According to one embodiment, the cosmetic composition of the invention is applied on the skin of a subject in need thereof, at least once a day.

According to one embodiment, the skin improvement method is for improving the complexion of a subject.

According to one embodiment, the skin improvement method is for matifying the skin of a subject.

Uses

The invention also relates to the use of the cosmetic pigment, preferably omniphobic, as defined above.

According to one embodiment, the omniphobicity of the cosmetic pigment of the invention long lasts the hold of said pigment on the skin of a subject.

According to one embodiment, the cosmetic pigment of the invention resists to sebum and/or sweat secreted by the skin of a subject.

According to one embodiment, the cosmetic pigment of the invention has not affinity (for water and/or oil. According to one embodiment, the cosmetic pigment of the invention has not affinity for oil such as cyclopentasiloxane (note as D5) or ester isononyl isononanoate.

According to one embodiment, the omniphobicity of the cosmetic pigment of the invention facilitates the deposit of the cosmetic pigment on the skin.

According to one embodiment, the cosmetic pigment of the invention is not toxic for human and/or the Environment.

EXAMPLES

The present invention is further illustrated by the following examples.

Abbreviations

° C.: Celsius degree
cP: centipoise
Da: dalton
D5: decamethylcyclopentasiloxane
h: hour
Hg: mercury
KOH: potassium hydroxide
M: mol per liter (mol/L)
mL: millimeter
$TiO_2$: titanium dioxide
μm: micrometer Materials and Methods All solvents and chitosan(s) were purchased from chemical company Sigma Aldrich. $TiO_2$ pigments with a mean diameter size of 40 μm were purchased from company Miyoshi France or from Sigma Aldrich. Three chitosans were studied and have the following characteristics:

|  | Chitosan A | Chitosan B | Chitosan C |
| --- | --- | --- | --- |
| Viscosity (cP) | 20-300 | 200-800 | 800-2000 |
| Deacetylation degree (%) | 75-85 | 75-85 | >75 |
| Mass average molar mass, Mw) (Da) | 50 000-190 000 | >190 000-310 000 | >310 000-375 000 |

Part 1—Chemistry Synthesis

Example 1: Process for Manufacturing the Omniphobic Pigments of the Invention

As a first step (step 1), an acidic aqueous solution of 100 mL comprising acetic acid, chitosan and dispersed $TiO_2$ particles, is prepared. The chitosan in the solution ranges from 1% to 10%, preferably is 3% or 10%, by weight to the total weight of chitosan and TiO₂ particles. The solution is magnetically stirred until complete dissolution of chitosan A, B or C.

Then, an aqueous solution of potassium hydroxide (1M) is added to the solution previously prepared at step 1 under pH-metric control. When the reaction medium has a pH of about 12, the addition of KOH is stopped and the reaction medium is stirred during 72 h.

Finally, the reaction medium is centrifuged and washed by centrifugation cycles with water. The pigment particles under the form of powder, are removed and dried under vacuum at a temperature ranging from 45° C. to 55° C. under a pressure lower than 50 mm Hg.

Tests are then performed for characterizing the chitosan adsorbed at the TiO₂ surface by thermogravimetry (ATG) and infra-red spectroscopy (ATR). The ATG results compared to those from TiO₂ particles without chitosan, evidence that the process of the invention provides a layer of chitosan adsorbed onto the surface of TiO₂ particles. Infrared spectra on the powder obtained by the process as defined above, evidence characteristic peaks of chitosan at 1100 cm$^{-1}$ and 3000 cm$^{-1}$.

Part 2—Physico-Chemical Tests

Example 2: Hydrophobic Character of the Pigment Obtained from the Process of the Invention The aim is to evidence that the pigment particles obtained by the process as defined in example 1 (i.e. a process comprising an alkalization step at pH=12), are hydrophobic compared to TiO₂ particles without any treatment, and compared to a process in which the alkalization step is carried out at pH=6, 7 or 10.

2.1. With Pigment Particles Obtained by the Process of the Invention (pH=12)

For this purpose, several powders have been dispersed in a vial containing pure water:
Sample 1: powder of TiO₂ particles without any treatment ["TiO₂"];
Sample 2: powder of TiO₂ particles on which are adsorbed chitosan A, said powder being washed once ["TiO₂+LV"];
Sample 3: powder of TiO₂ particles on which are adsorbed chitosan A, said powder being washed four times ["TiO₂+LV×4"];
Sample 4: powder of TiO₂ particles on which are adsorbed chitosan B, said powder being washed once ["TiO₂+MV"];
Sample 5: powder of TiO₂ particles on which are adsorbed chitosan B, said powder being washed four times ["TiO₂+MV×4"].

The results presented in FIG. 1, show that:
when TiO₂ particles are not coated with chitosan, the particles are homogenously dispersed in water and show an hydrophilic character; and
when TiO₂ particles are coated with chitosan, whatever the chitosan A, B or C, the particles are coagulating because of their hydrophobicity and are sedimenting at the bottom of vials under the form of a white powder.

Consequently, this experiment evidences that the process of the invention provides hydrophobic pigment particles contrary to uncoated TiO₂ particles.

2.2. Comparison with Particles Obtained at pH=6 or 7

The same experiment than paragraph 2.1. was carried out with particles obtained from a process having an alkalization step at pH 6 or 7, and compared to those obtained from the process of the invention (alkalization step at pH 12).

Figure 2:
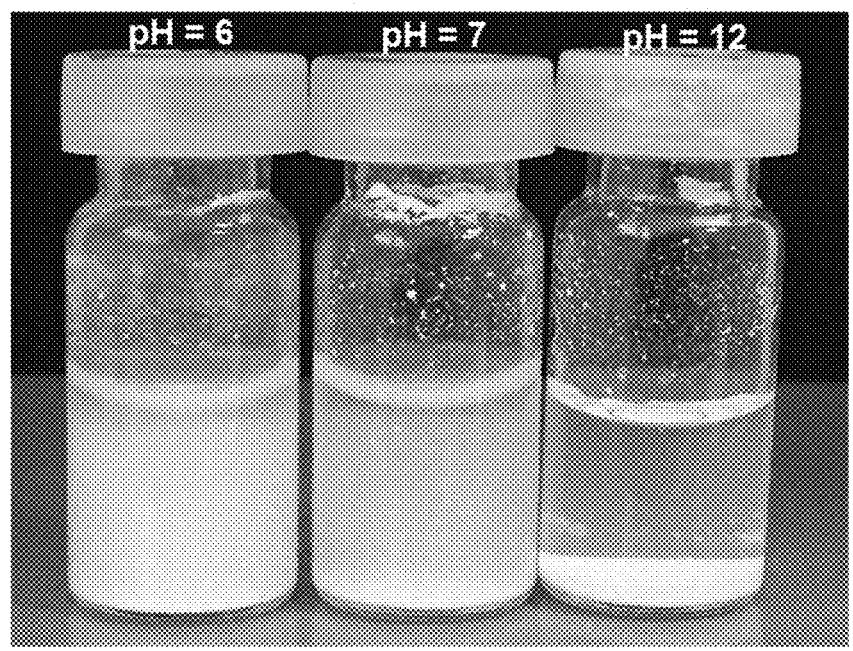
FIG. 2 is a photograph showing vials containing pure water and: TiO$_2$ particles coated with chitosan obtained from a process having an alkalization at pH (from left to right) of 6, 7 or 12 (process of the invention).

The results presented in FIG. 2, show that the particles of the invention are hydrophobic contrary to those obtained by a process in which the alkalization step is carried out at pH=6 or 7 where in FIG. 2 it is clear that the particles are still dispersed in solution because of hydrophilicity.

2.3. Comparison with Particles Obtained at pH=10

The comparison in water between particles obtained from a process having an alkalization step at pH of 10 and an equal mass ratio of TiO₂ and chitosan, and those obtained from the process of the invention (alkalization step at pH 12) has been also carried out.

First, it was observed that the final products between the two processes are different: the process with a step at pH of 10 leads to a solid pink material, compact and difficult to grind whereas the product obtained by the process of the invention leads to a particulate material under the form of a white powder.

The behavior of these products in water are also different:
the product of the process having an alkalization step at pH of 10, keeps under the form of solid blocks; and
the product of the process of the invention is under the form of hydrophobic individualized white particles (powder).

Consequently, this experiment evidences that the process of the invention provides hydrophobic pigment particles contrary to a process having a step at pH of 10 at equimolar concentrations. Indeed, the product obtained from a process with a step at pH of 10, is not compatible with a cosmetic use as a pigment that requires the form of a powder, such as the present invention.

Example 3: Oleophobic Character of the Pigment Obtained from the Process of the Invention The aim is to evidence that the pigment particles obtained by the process as defined in example 1 (i.e. a process comprising an alkalization step at pH=12), are oleophobic compared to TiO₂ particles without any treatment, and compared to a process in which the alkalization step is carried out at pH=6, 7 or 10.

3.1. With Pigment Particles Obtained by the Process of the Invention (pH=12)

For this purpose, several powders have been dispersed in a vial containing a mixture of pure water and ester isononyl isononanoate:
Sample 1: powder of TiO₂ particles without any treatment ["TiO₂"];
Sample 2: powder of TiO₂ particles on which are adsorbed chitosan A, said powder being washed once ["TiO₂+LV"];
Sample 3: powder of TiO₂ particles on which are adsorbed chitosan A, said powder being washed four times ["TiO₂+LV×4"];
Sample 4: powder of TiO₂ particles on which are adsorbed chitosan B, said powder being washed once ["TiO₂+MV"];
Sample 5: powder of TiO₂ particles on which are adsorbed chitosan B, said powder being washed four times ["TiO₂+MV×4"].

Figure 3:
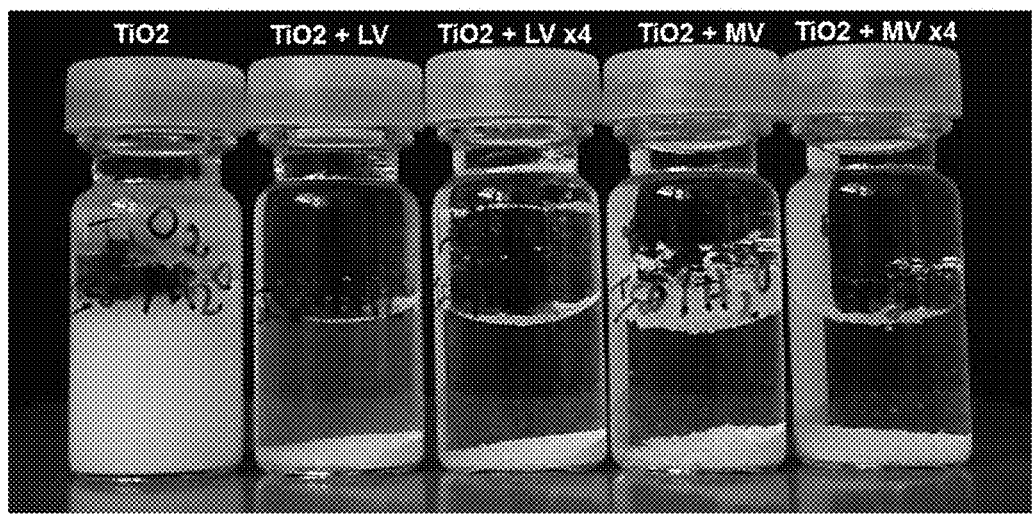
FIG. 3 is a photograph showing from left to right, vials containing a mixture of pure water and ester isononyl isononanoate, and: uncoated TiO$_2$ particles [TiO$_2$]; TiO$_2$ particles coated with chitosan A and washed once [TiO$_2$+LV]; TiO$_2$ particles coated with chitosan A and washed four times [TiO$_2$+LV×4]; TiO$_2$ particles coated with chitosan B and washed once [TiO$_2$+MV] and TiO$_2$ particles coated with chitosan B and washed four times [TiO$_2$+MV×4].

The results presented in FIG. 3, show that:
when TiO₂ particles are not coated with chitosan, the particles are homogenously dispersed in water exclusively: only some of them are coating the walls of the upper oil phase (ester isononyl isononanoate); and
when TiO₂ particles are coated with chitosan, whatever the chitosan A, B or C, the particles are excluded from both phases of water and ester isononyl isononanoate, and settled down to the bottom of vials under the form of a white powder.

Consequently, this experiment evidences that the process of the invention provides hydrophobic and oleophobic pigment particles contrary to uncoated $TiO_2$ particles.

3.2. Comparison with Particles Obtained at pH=6 or 7

The same experiment than paragraph 3.1. was carried out with particles obtained from a process having an alkalization step at pH 6 or 7, and compared to those obtained from the process of the invention (alkalization step at pH 12).

As for water, contrary to those obtained by a process in which the alkalization step is carried out at pH=6 or 7, particles are not hydrophobic (presence in the water phase) contrary to the results of the invention where particles are shown to be both hydrophobic and oleophobic.

3.3. Comparison with Particles Obtained at pH=10

The same experiment than paragraph 3.1. was carried out with particles obtained from a process having an alkalization step at pH 10 at equimass concentration of chitosan and $TiO_2$, and compared to those obtained from the process of the invention (alkalization step at pH 12).

As for water, the results show that the particles of the invention stay under a powder form and are both hydrophobic and oleophobic contrary to those obtained by a process in which the alkalization step is carried out at pH=10 for which the product appears either on blocks or under the form of cotton, impossible to transform into a pigment useful for cosmetic applications.

The invention claimed is:

1. A process for manufacturing an omniphobic cosmetic pigment, said process comprising:
    preparing an acidic aqueous solution comprising metal oxide particles and a poly(β-(1→4)-D-glucosamine), said poly(β-(1→4)-D-glucosamine) being acetylated, or partially or totally deacetylated; and
    (ii) increasing the pH until about 12, of the solution obtained at step (i) in order to obtain the adsorption of said poly (β-(1→4)- D-glucosamine) on the metal oxide particles and the precipitation of the resulting metal oxide particles coated with said poly(β-(1→4)-D-glucosamine).

2. The process according to claim 1, wherein the metal oxide particles are selected from the group consisting of titanium oxide, iron oxide, zinc oxide, zirconium oxide, yellow iron oxide, black iron oxide, red iron oxide, chromium oxide, chromium hydroxide, ultramarine, and silicates.

3. The process according to claim 1, wherein the metal oxide particles have a size ranging from 100 nm to 100 μm.

4. The process according to claim 1, wherein the poly(β-(1→4)-D-glucosamine) is either totally deacetylated or both deacetylated and acetylated.

5. The process according to claim 1, wherein the poly(β-(1→4)-D-glucosamine) has a viscosity measured at about 25° C., ranging from 10 cP to 2000 cP.

6. The process according to claim 4, wherein the poly(β-(1→4)-D-glucosamine) is partially deacetylated and has a deacetylation degree ranging from 70% to 99%.

7. The process according to claim 1, wherein the poly(β-(1→4)-D-glucosamine) has a mass average molar mass (Mw) ranging from 40 000 Da to 500 000 Da.

8. The process according to claim 1, wherein the amount of the poly (β-(1→4)-D-glucosamine) ranges from more than 0% to 20% by weight to the total weight of said poly (β-(1→4)-D-glucosamine) and metal oxide particles.

9. An omniphobic cosmetic pigment obtained by the process according to claim 1.

10. The omniphobic cosmetic pigment of claim 9, comprising or consisting of titanium oxide particles on which are adsorbed chitosan chains.

11. A cosmetic composition comprising the omniphobic cosmetic pigment according to claim 9 and a cosmetically acceptable base.

12. The composition according to claim 11, wherein the cosmetically acceptable base is anhydrous.

13. The composition according to claim 11, which is an aqueous gel, an oily gel, a paste, a cream, a lotion, a milk, a stick, a soap, a foam, a shampoo, a compact powder, a loose powder, a nail polish, a beauty mask, an aerosol, a film, a serum, an emulsion, or a patch.

14. A cosmetic skin improvement method comprising administering to a subject in need thereof the omniphobic cosmetic pigment according to claim 9, or a cosmetic composition comprising said omniphobic cosmetic pigment and a cosmetically acceptable base.

15. The skin improvement method according to claim 14, wherein the composition is administered to the skin of a subject in need thereof, once per day.

16. A composition for make-up, skincare, sun care, haircare, nail polish, toiletries, baby care or pet care, comprising the cosmetic composition of claim 11.

17. The process according to claim 4, wherein the poly (β-(1→4)-D-glucosamine) is chitosan.

18. The process according to claim 2, wherein the silicates are selected from the group consisting of mica, sericite, kaolin, talc, aluminium silicate, magnesium silicate, calcium silicate and clay.

* * * * *